United States Patent [19]

Rosenbluth et al.

[11] Patent Number: 6,015,424
[45] Date of Patent: Jan. 18, 2000

[54] APPARATUS AND METHOD FOR VASCULAR EMBOLIZATION

[75] Inventors: Robert F. Rosenbluth; Brian J. Cox, both of Laguna Niguel; George R. Greene, Jr., Costa Mesa, all of Calif.

[73] Assignee: MicroVention, Inc., Aliso Viejo, Calif.

[21] Appl. No.: 09/069,008

[22] Filed: Apr. 28, 1998

[51] Int. Cl.$^7$ ............................................. A61M 29/00
[52] U.S. Cl. ........................... 606/200; 606/194; 623/1
[58] Field of Search ................................ 606/108, 200, 606/191, 194; 623/1

[56]  References Cited

U.S. PATENT DOCUMENTS

| | | | |
|---|---|---|---|
| 4,551,132 | 11/1985 | Pásztor et al. | 604/52 |
| 4,795,741 | 1/1989 | Leshchiner et al. | 514/21 |
| 4,819,637 | 4/1989 | Dormandy, Jr. et al. | 128/325 |
| 4,994,069 | 2/1991 | Ritchart et al. | 606/191 |
| 5,133,731 | 7/1992 | Butler et al. | 606/191 |
| 5,163,952 | 11/1992 | Froix | 623/1 |
| 5,226,911 | 7/1993 | Chee et al. | 606/191 |
| 5,312,415 | 5/1994 | Palermo | 606/108 |
| 5,350,397 | 9/1994 | Palermo et al. | 606/200 |
| 5,382,259 | 1/1995 | Phelps et al. | 606/151 |
| 5,382,260 | 1/1995 | Dormandy, Jr. et al. | 606/151 |
| 5,443,478 | 8/1995 | Purdy | 606/200 |
| 5,469,867 | 11/1995 | Schmitt | 128/898 |
| 5,476,472 | 12/1995 | Dormandy, Jr. et al. | 606/151 |

(List continued on next page.)

FOREIGN PATENT DOCUMENTS

| | | | |
|---|---|---|---|
| 97/26939 | 7/1997 | WIPO | A61M 29/00 |
| 97/27888 | 8/1997 | WIPO | A61M 1/00 |

OTHER PUBLICATIONS

Schmutz F. et al., "Embolization of Cerebral Arteriovenous Malformations with Silk: Histopathologic Changes and Hemorrhagic Complications," *AJNR AM J Neuroradial* (Aug. 1997) vol. 18, pp. 1233–1237.

Graves V. B. et al., "Endovascular Occlusion of the Carotid or Vertebral Artery with Temporary Proximal Flow Arrest and Microcoils: Clinical Results," *AJNR Am J Neuroradial* (Aug. 1997) vol. 18, pp. 1201–1206.

Viñuela F. et al., "Gugleilmi detachable coil embolization of acute intracranial aneurysm; perioperative anatomical and clinical outcome in 403 patients," *J Neurosurg* (Mar. 1997) vol. 86, pp. 475–482.

Hagashida R. T., M.D. et al., "Interventional Treatment of Intracranial Aneurysms," pp. 460–463.

*Primary Examiner*—Michael Buiz
*Assistant Examiner*—Julian W. Woo
*Attorney, Agent, or Firm*—Klein & Szekeres, LLP

[57]  ABSTRACT

Apparatus for vascular embolization, deployable through a microcatheter, includes a flexible, elongate deployment tube dimensioned for insertion through the microcatheter, and a filamentous embolic device releasably attached to the distal end of the tube. The embolic device is controllably transformable from a soft, compliant state to a rigid or semi-rigid state. The embolic device may include a polymeric material that is transformable by contact with vascular blood or with a liquid that is cooler than vascular blood, or it may include a metallic material that is transformable by electrolytic corrosion. The embolic device may be a continuous filamentous polymeric extrusion; an elongate microcoil filled with polymeric material; an elongate, multi-segmented chain including polymeric interconnecting portions; or an elongate chain of metal segments that are fused together by electrolytic corrosion. An aneurysm is embolized with this apparatus by deploying a microcatheter so that its distal end is adjacent the aneurysm; deploying the embolic device through the microcatheter and into the aneurysm so that the embolic device forms a web-like mass in the aneurysm; and transforming the embolic device from its soft, compliant state to its rigid or semi-rigid state. The embolic device is advantageously deployed by releasably attaching it to a flexible, elongate deployment tube that is passed through the microcatheter, and then detaching the embolic device from the tube when the embolic device is suitably situated.

34 Claims, 2 Drawing Sheets

U.S. PATENT DOCUMENTS

| | | | |
|---|---|---|---|
| 5,525,334 | 6/1996 | Ito et al. | 424/78.35 |
| 5,578,074 | 11/1996 | Mirigian | 623/1 |
| 5,580,568 | 12/1996 | Greff et al. | 424/423 |
| 5,582,619 | 12/1996 | Ken | 606/191 |
| 5,612,050 | 3/1997 | Rowe et al. | 424/423 |
| 5,624,461 | 4/1997 | Mariant | 606/191 |
| 5,624,685 | 4/1997 | Takahashi et al. | 424/488 |
| 5,634,936 | 6/1997 | Linden et al. | 606/213 |
| 5,645,558 | 7/1997 | Horton | 606/191 |
| 5,658,308 | 8/1997 | Snyder | 606/191 |
| 5,718,711 | 2/1998 | Berenstein et al. | 606/191 |
| 5,725,568 | 3/1998 | Hastings | 623/1 |
| 5,749,894 | 5/1998 | Engelson | 606/213 |

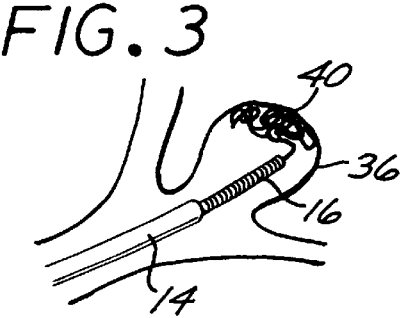
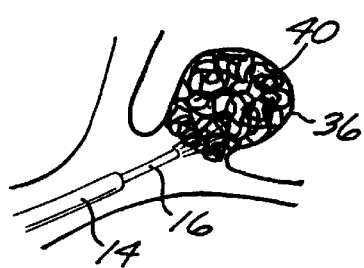
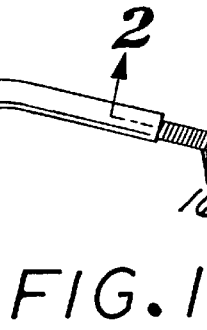
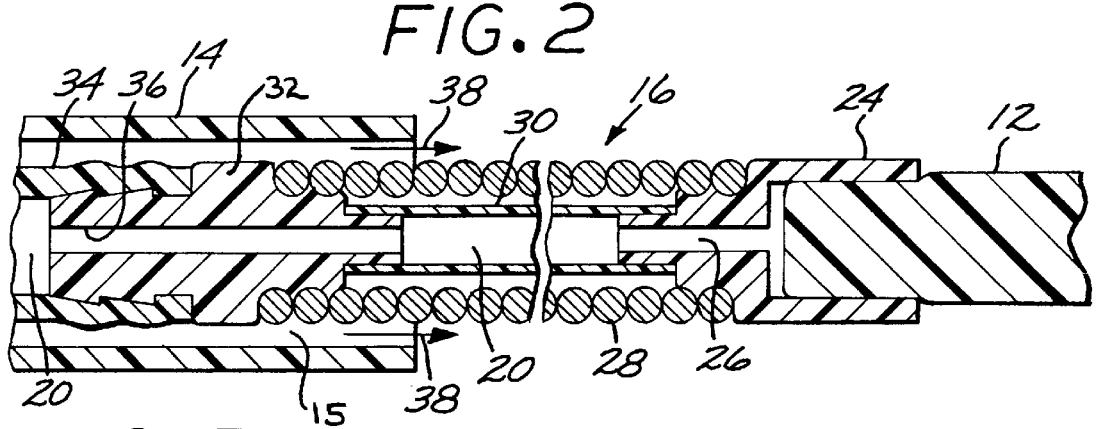
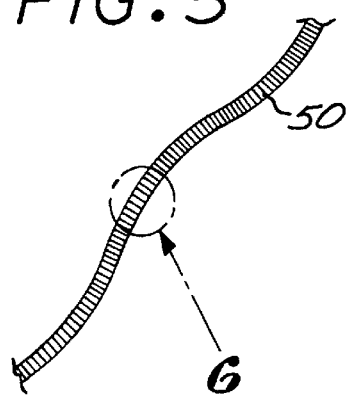
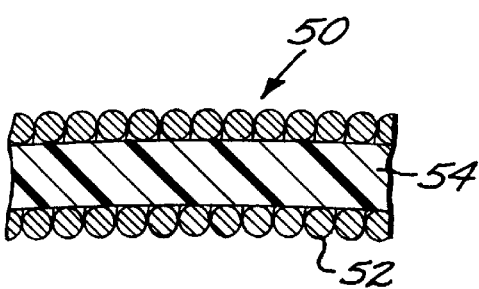

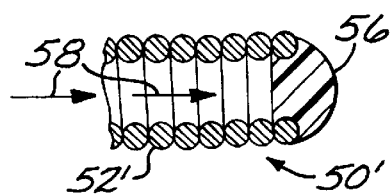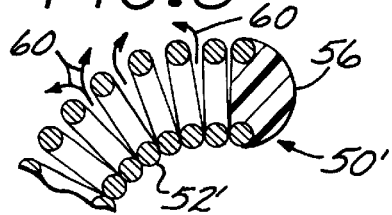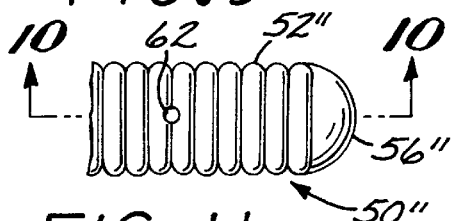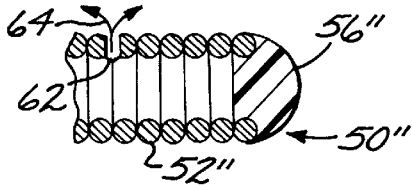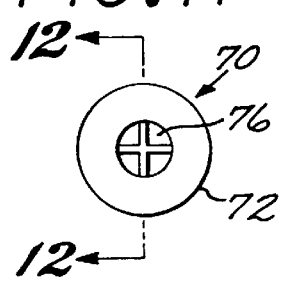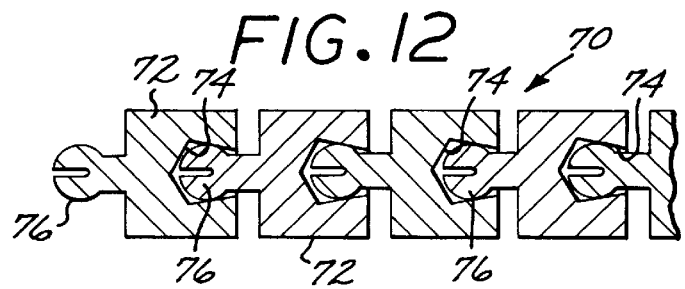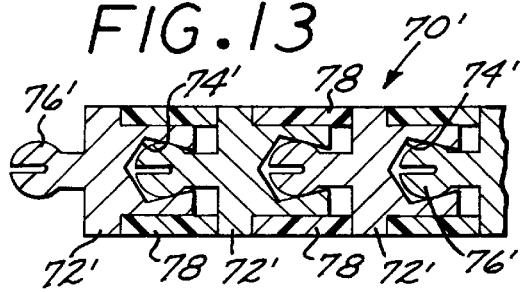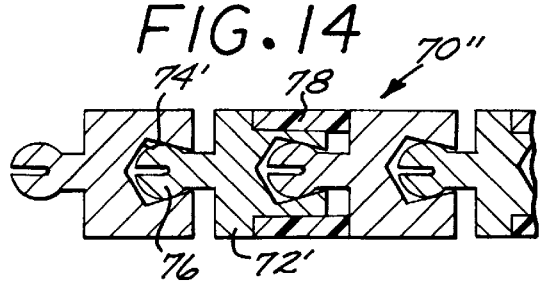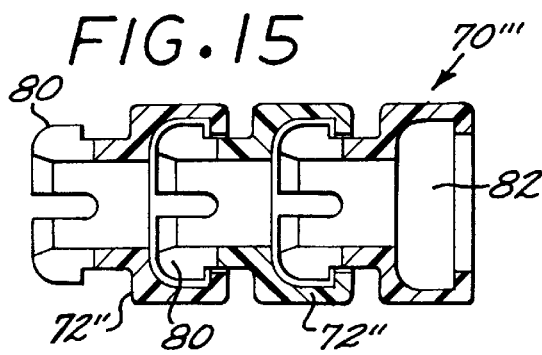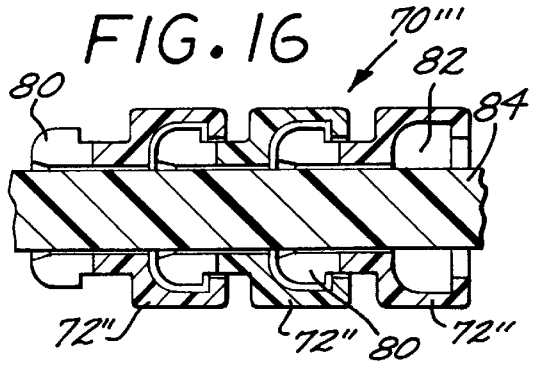

APPARATUS AND METHOD FOR VASCULAR EMBOLIZATION

CROSS-REFERENCE TO RELATED APPLICATIONS

Not Applicable

FEDERALLY-SPONSORED RESEARCH OR DEVELOPMENT

Not Applicable

BACKGROUND OF THE INVENTION

This invention relates generally to the field of vascular occlusion devices and methods. More specifically, it relates to an apparatus and method for occluding a blood vessel by embolizing a targeted site (such as an aneurysm) in the blood vessel.

The embolization of blood vessels is desired in a number of clinical situations. For example, vascular embolization has been used to control vascular bleeding, to occlude the blood supply to tumors, and to occlude vascular aneurysms, particularly intracranial aneurysms. In recent years, vascular embolization for the treatment of aneurysms has received much attention. Several different treatment modalities have been employed in the prior art. U.S. Pat. No. 4,819,637—Dormandy, Jr. et al., for example, describes a vascular embolization system that employs a detachable balloon delivered to the aneurysm site by an intravascular catheter. The balloon is carried into the aneurysm at the tip of the catheter, and it is inflated inside the aneurysm with a solidifying fluid (typically a polymerizable resin or gel) to occlude the aneurysm. The balloon is then detached from the catheter by gentle traction on the catheter. While the balloon-type embolization device can provide an effective occlusion of many types of aneurysms, it is difficult to retrieve or move after the solidifying fluid sets, and it is difficult to visualize unless it is filled with a contrast material. Furthermore, there are risks of balloon rupture during inflation and of premature detachment of the balloon from the catheter.

Another approach is the direct injection of a liquid polymer embolic agent into the vascular site to be occluded. One type of liquid polymer used in the direct injection technique is a rapidly polymerizing liquid, such as a cyanoacrylate resin, particularly isobutyl cyanoacrylate, that is delivered to the target site as a liquid, and then is polymerized in situ. Alternatively, a liquid polymer that is precipitated at the target site from a carrier solution has been used. An example of this type of embolic agent is a cellulose acetate polymer mixed with bismuth trioxide and dissolved in dimethyl sulfoxide (DMSO). Another type is ethylene glycol copolymer dissolved in DMSO. On contact with blood, the DMSO diffuses out, and the polymer precipitates out and rapidly hardens into an embolic mass that conforms to the shape of the aneurysm. Other examples of materials used in this "direct injection" method are disclosed in the following U.S. Pat. Nos.: 4,551,132—Pásztor et al.; 4,795,741—Leshchiner et al.; 5,525,334—Ito et al.; and 5,580,568—Greff et al.

The direct injection of liquid polymer embolic agents has proven difficult in practice. For example, migration of the polymeric material from the aneurysm and into the adjacent blood vessel has presented a problem. In addition, visualization of the embolization material requires that a contrasting agent be mixed with it, and selecting embolization materials and contrasting agents that are mutually compatible may result in performance compromises that are less than optimal. Furthermore, precise control of the deployment of the polymeric embolization material is difficult, leading to the risk of improper placement and/or premature solidification of the material. Moreover, once the embolization material is deployed and solidified, it is difficult to move or retrieve.

Another approach that has shown promise is the use of thrombogenic microcoils. These microcoils may be made of a biocompatible metal alloy (typically platinum and tungsten) or a suitable polymer. If made of metal, the coil may be provided with Dacron fibers to increase thrombogenicity. The coil is deployed through a microcatheter to the vascular site. Examples of microcoils are disclosed in the following U.S. Pat. Nos.: 4,994,069—Ritchart et al.; 5,133,731—Butler et al.; 5,226,911—Chee et al.; 5,312,415—Palermo; 5,382,259—Phelps et al.; 5,382,260—Dormandy, Jr. et al.; 5,476,472—Dormandy, Jr. et al.; 5,578,074—Mirigian; 5,582,619—Ken; 5,624,461—Mariant; 5,645,558—Horton; 5,658,308—Snyder; and 5,718,711—Berenstein et al.

The microcoil approach has met with some success in treating small aneurysms with narrow necks, but the coil must be tightly packed into the aneurysm to avoid shifting that can lead to recanalization. Microcoils have been less successful in the treatment of larger aneurysms, especially those with relatively wide necks. A disadvantage of microcoils is that they are not easily retrievable; if a coil migrates out of the aneurysm, a second procedure to retrieve it and move it back into place is necessary. Furthermore, complete packing of an aneurysm using microcoils can be difficult to achieve in practice.

A specific type of microcoil that has achieved a measure of success is the Guglielmi Detachable Coil ("GDC"). The GDC employs a platinum wire coil fixed to a stainless steel guidewire by a solder connection. After the coil is placed inside an aneurysm, an electrical current is applied to the guidewire, which heats sufficiently to melt the solder junction, thereby detaching the coil from the guidewire. The application of the current also creates a positive electrical charge on the coil, which attracts negatively-charged blood cells, platelets, and fibrinogen, thereby increasing the thrombogenicity of the coil. Several coils of different diameters and lengths can be packed into an aneurysm until the aneurysm is completely filled. The coils thus create and hold a thrombus within the aneurysm, inhibiting its displacement and its fragmentation.

The advantages of the GDC procedure are the ability to withdraw and relocate the coil if it migrates from its desired location, and the enhanced ability to promote the formation of a stable thrombus within the aneurysm. Nevertheless, as in conventional microcoil techniques, the successful use of the GDC procedure has been substantially limited to small aneurysms with narrow necks.

There has thus been a long-felt, but as yet unsatisfied need for an aneurysm treatment device and method that can substantially fill aneurysms of a large range of sizes, configurations, and neck widths with a thrombogenic medium with a minimal risk of inadvertent aneurysm rupture or blood vessel wall damage. There has been a further need for such a method and device that also allow for the precise locational deployment of the medium, while also minimizing the potential for migration away from the target location. In addition, a method and device meeting these criteria should also be relatively easy to use in a clinical setting. Such ease of use, for example, should preferably include a provision for good visualization of the device during and after deployment in an aneurysm.

SUMMARY OF THE INVENTION

Broadly, one aspect of the present invention is an embolic device, comprising a thrombogenic medium, that is deployed in a soft, compliant state, and that is controllably transformed into a rigid or semi-rigid state after deployment. In another aspect, the present invention is an apparatus for deploying the aforesaid embolic device in the interior of an aneurysm. Still another aspect of the present invention is a method for embolizing a vascular site, particularly an aneurysm, using the aforesaid embolic device.

In a first preferred embodiment, the embolic device comprises a continuous, filamentous extrusion of polymeric "transition material" that is inserted into an aneurysm while in a soft, self-adherent, compliant state. The insertion of one or more such embolic devices results in a mass of material that substantially fills the aneurysm and that substantially conforms to the interior shape of the aneurysm. Depending on the particular polymeric material employed, any of several mechanisms is then employed controllably to transform the transition material into a rigid or semi-rigid state, in which the material forms a stable, thrombogenic "plug" inside the aneurysm. For example, the material may be injected at a temperature slightly above body temperature and then cooled into its rigid or semi-rigid state by contact with the patient's blood, or by the injection of a cooler saline solution. Alternatively, the polymeric material may be exposed to a hardening agent that reacts physically or chemically with the material to effect the transition to the rigid or semi-rigid state. As still another alternative, the polymeric material may be mixed with a water soluble, biocompatible plasticizer that dissolves out in the vascular blood to leave a rigid or semi-rigid polymeric structure.

In another preferred embodiment, the embolic device comprises an elongate, flexible microcoil, the interior of which contains the transition material. The microcoil is deployed in the aneurysm with the transition material in its soft, compliant state, and then the transition material is rigidified by any suitable mechanism, as mentioned above, thereby rigidifying the microcoil in situ.

In another preferred embodiment, the embolic device comprises an elongate, flexible chain of articulated segments linked together so as to form a limp segmented filament that is installed in the aneurysm. After placement in the aneurysm, the segmented filament is rigidized by fusing the segments through one of several mechanisms, depending on the material of the segments. For example, if the segments are metal, the segments can be fused together by electrolytic corrosion resulting from a current being passed through the device. If the segments are made, at least in part, of a polymeric "transition material", the transition of the device to a rigid or semi-rigid state can be induced by one of the mechanisms discussed above.

In still another preferred embodiment, the embolic device is a highly-compliant chain-like structure comprising a plurality of interconnected hollow links or segments. Each of the segments has a slotted, mushroom-shaped head portion and a socket portion that is shaped and dimensioned to receive the head portion of an adjacent segment. The hollow segments allow the embolic device to be inserted into an aneurysm over a guide wire (not shown), if desired. Once the device is inserted, a polymeric transition material is injected, while in the soft, compliant state, into the hollow interior of the device, and the transformation into its rigid or semi-rigid state can be effected as described above. Alternatively, the segments can be made of a metal and then fused together by electrolytic corrosion.

A preferred embodiment of the apparatus for deploying the embolic device comprises a flexible, elongate, hollow deployment tube having an axial passage and a cup-shaped holding element at its distal end. The holding element, which is configured and dimensioned to hold the proximal end of the embolic device by a frictional engagement, has a base with an opening that communicates with the axial lumen. The deployment tube (or at least its distal end) is preferably made of a radiopaque material, such as a biocompatible metal alloy, thereby facilitating visualization during the deployment of the embolic device, without requiring the inclusion of a radiopaque substance in the embolic device itself.

The preferred method of deploying the embolic device using this apparatus is as follows: The deployment tube, with the embolic device thus attached to it, is inserted into and pushed through a microcatheter that has been advanced intravascularly to the aneurysm site by means well known in the surgical arts. Passage of the flexible deployment tube and the limp embolic device through the microcatheter is assisted and facilitated by a flow of fluid (e.g., saline solution) through the microcatheter around the exterior of the deployment tube and the embolic device. The deployment tube is pushed through the microcatheter until the embolic device has been fully inserted into the aneurysm. Finally, a fluid (e.g., saline solution) is injected through the axial lumen and into the holding element of the deployment tube. The pressure of the fluid pushes the embolic device out of the holding element, thereby detaching the embolic device from the deployment tube. The deployment tube is then withdrawn from the microcatheter. If more than one embolic device is necessary to fill the aneurysm, the above-described process can be repeated until the aneurysm is filled.

The present invention offers a number of advantages over prior art embolization methods and devices. For example, the embolic device of the present invention is deployable within an aneurysm in a soft, compliant state, thereby minimizing the risk of aneurysm rupture or vascular damage. The location of the embolic device can be controlled with some precision, and, until it is detached from the deployment tube, its deployment can be reversed. Thus, the risks of migration out of the aneurysm are minimized. Furthermore, the embolic device of the present invention can be used in aneurysms having a wide variety of shapes and sizes; it is not limited to small aneurysms or those with narrow necks. These and other advantages of the present invention will be more fully appreciated from the detailed description that follows.

BRIEF DESCRIPTION OF THE DRAWINGS

FIG. 1 is an elevational view of a preferred embodiment of an apparatus for deploying an embolic device in accordance with the present invention;

FIG. 2 is a cross-sectional view taken along line 2—2 of FIG. 1, showing the apparatus with an embolic device in accordance with a first preferred embodiment of the present invention;

FIGS. 3 and 4 are idealized views of an embolic device in accordance with present invention in the process of being deployed in an aneurysm by means of the apparatus of FIGS. 1 and 2;

FIG. 5 is an elevational view of one embodiment of an embolic device in accordance with a second preferred embodiment of the present invention;

FIG. 6 is a detailed view taken within the area of FIG. 5 designated by the broken outline 6;

FIG. 7 is an elevational view of a portion of an embolic device that is a modification of the embodiment of FIGS. 5 and 6;

FIG. 8 is a cross-sectional view taken along line 8—8 of FIG. 7;

FIG. 9 is an elevational view of a portion of an embolic device that is another modification of the embodiment of FIGS. 5 and 6;

FIG. 10 is a cross-sectional view taken along line 10—10 of FIG. 9;

FIG. 11 is an end elevational view of an embolic device in accordance with a third preferred embodiment of the present invention;

FIG. 12 is a cross-sectional view taken along line 10—10 of FIG. 11; and

FIGS. 13–16 are cross-sectional views, similar to that of FIG. 10, showing further modifications of the third preferred embodiment of the embolic device of the present invention.

DETAILED DESCRIPTION OF THE INVENTION

FIGS. 1 and 2 illustrate a preferred embodiment of an apparatus 10 for deploying an embolic device 12 in accordance with the present invention. The apparatus 10 comprises a microcatheter 14 having an axial lumen 15, and a deployment tube 16 that is insertable through the lumen 15 of the microcatheter 14. The microcatheter 14 is of conventional design, and many suitable microcatheters for the apparatus 10 are commercially available. The proximal end of the microcatheter 14 is provided with a fitting 18 for coupling to a source (not shown) of a fluid (such as saline solution), the flow of which is used to facilitate the passage of the deployment tube 16 through the microcatheter 14, as will be described below. The microcatheter 14, or at least its distal end, is preferably made of a radiopaque material, such as a biocompatible metal. Alternatively, it may be made of a suitable plastic, with a radiopaque insert (not shown) proximate its distal end, as is well known in the art.

The deployment tube 16 is a long, thin, hollow, highly flexible tube, having an axial passage 20 and an overall length that is somewhat greater than that of the microcatheter 14. The deployment tube 16 has a proximal end to which is attached an inlet fitting 22 that communicates with the axial passage 20 and that is adapted for coupling to a liquid source (not shown). The source contains a biocompatible liquid that can be delivered to the inlet fitting 22 under pressure for purposes to be described below. The distal end of the deployment tube 16 is provided with a cup-like fitting 24 that serves as a holding element that is configured for frictional engagement with the proximal end of the embolic device 12. The interior of the holding element 24 communicates with the axial passage 20 of the deployment tube 16 by means of an axial bore 26. A substantial portion of the length of the deployment tube 16 extending proximally from the holding element 24 is formed as a highly flexible and compliant outer portion 28 formed from a continuous length of helically- coiled metal wire. The outer portion 28 concentrically surrounds an inner portion 30, formed from a highly-flexible polymeric material, the interior of which defines a distal portion of the axial passage 20 that is coupled to the axial bore 26 of the holding element 24. The proximal ends of both the outer portion 28 and the inner portion 30 are connected to the distal end of an internal transition fitting 32, the proximal end of which is connected to the distal end of a proximal tube section 34, which may be made of a flexible polymeric material. An axial bore 36 traverses the length of the transition fitting 32, providing fluid communication between the distal portion of the axial passage 20 that is within the inner portion 30, and the proximal portion of the axial passage 20 that is defined within the proximal tube section 34. The aforementioned inlet fitting 22 is connected to the proximal end of the proximal tube section 34.

As shown in FIGS. 1 and 2, the embolic device 12 comprises a continuous, filamentous extrusion of polymeric "transition material". This transition material is initially in a soft, self-adherent, compliant state. While the material is in this state, the embolic device 12 is inserted into an aneurysm. The insertion results in a web-like mass of material that substantially fills the aneurysm and that substantially conforms to the interior shape of the aneurysm. Depending on the particular polymeric material employed, any of several mechanisms is then employed controllably to transform the transition material into a rigid or semi-rigid state, in which the material forms a stable, thrombogenic "plug" inside the aneurysm. For example, the embolic device 12 may be injected at a temperature slightly above body temperature and then cooled into its rigid or semi-rigid state by contact with the patient's vascular blood, or by the injection of a cooler saline solution. Alternatively, the polymeric material may be exposed to a hardening agent that reacts chemically or physically with the material to effect the transition to the rigid or semi-rigid state. As still another alternative, the polymeric material may be mixed with a water-soluble, biocompatible plasticizer (as described below) that dissolves out in the vascular blood to leave a rigid or semi-rigid polymeric structure.

Prior to deployment, and while the material of the embolic device 12 is in its initial soft, compliant state, the proximal end of the embolic device 12 is pushed into the holding element 24 of the deployment tube 16, where it is frictionally retained in place. With the distal end of the microcatheter 14 having previously been deployed adjacent the targeted aneurysm (designated by the numeral 36 in FIGS. 3 and 4), the distal end (not shown) of the embolic device 12 is then inserted into the fitting 18 at the proximal end of the microcatheter 14. As the embolic device 12 and the deployment tube 16 are pushed through the lumen 15 of the microcatheter 14, a liquid, such as a saline solution, is caused to flow through the microcatheter 14, as indicated by arrows designated by the numeral 38 in FIG. 2. The flow of the liquid assists in carrying the embolic device 12 and the deployment tube 16 through the microcatheter 14 until the distal end of the deployment tube 16 is well within the aneurysm 36 (FIG. 3), at which point the embolic device 12 starts to form a web-like, thrombogenic mass or plug 40 within the aneurysm. The proximal end of the embolic device 12 is detached from the deployment tube 16 by the pressure of a fluid (such as saline solution) injected through the axial passage 20 of the deployment tube and the axial bore 26 of the holding element 24.

If the size of the aneurysm 36 requires more than one embolic device 12 to fill it completely, the deployment tube 16 is withdrawn through the microcatheter 14 and reloaded with another embolic device 12, and the above-described deployment process is repeated as often as is needed to fill the aneurysm 36 completely (FIG. 4). As shown in FIG. 4, the final embolic device 12 is then detached from the deployment tube 16 in the manner described above, and the deployment tube 16 is withdrawn from the microcatheter 14.

The fluid used to carry the deployment tube 16 and the embolic device 12 through the microcatheter 14, and the fluid used to detach the embolic device 12 from the deployment tube (i.e., the "deployment fluids"), are selected so that they do not effect the transition of the embolic device material from its soft state to its rigid or semi-rigid state. Thus, for example, if the transition material effects the transition by being cooled from slightly above body temperature (e.g., from about 40° C.) to approximately normal body temperature (37° C.), these deployment fluids are injected at about the higher temperature, so that the transition does not take place prematurely.

Once the web-like thrombogenic mass 40 completely fills the aneurysm 36, as shown in FIG. 4, the transition material of the embolic device(s) 12 installed within the aneurysm 36 can be transformed to its rigid or semi-rigid state by means of one of the aforementioned mechanisms, depending on the nature of the material itself. For example, a "transition fluid", such as saline at the required temperature, can be injected through the microcatheter 14 to bathe the mass 40, thereby effecting the desired transition.

FIGS. 5 and 6 illustrate an embolic device 50 in accordance with a second preferred embodiment of the invention. The embolic device 50 comprises a hollow metal microcoil 52, the interior of which is filled with a core 54 of polymeric transition material. The embolic device 50 is rigidified by the transformation of the material of the core 54 from its soft, compliant state to its rigid or semi-rigid state effecting a temperature change, as described above. The deployment of the embolic device 50 is performed by essentially the same method as that used for the deployment of the previously-described embodiment.

Modifications of the embolic device 50 are shown in FIGS. 7 through 10. In FIGS. 7 and 8, an embolic device 50' comprises a hollow metal microcoil 52', the distal end of which is closed by an end cap 56. The device 50' lacks a core. Instead, when the microcoil 52' is inserted into an aneurysm, but before it is detached from the deployment tube 16, a flowable transition material is injected into the interior of the microcoil 52' through the axial passage 20 of the deployment tube 16 and the axial bore 26 of the holding element 24. The injection of the transition material is illustrated in FIG. 7 by the arrows designated by the numeral 58. The flexing and bending of the installed microcoil 52', as shown in FIG. 8, causes interstices between the coils to open up, allowing the transition material to flow out of the microcoil, as indicated by the arrows designated by the numeral 60. The transition material then can be transformed into its rigid or semi-rigid state, thereby rigidifying the microcoil 52'. The exposed transition material that has flowed out of the interstices between the coils provides further rigidity and enhances the thrombogenicity of the device 50'.

The advantages of the embolic device 50' of FIGS. 7 and 8 can also be realized in another modification shown in FIGS. 9 and 10. In this latter modification, an embolic device 50" comprises a hollow metal microcoil 52" having an end cap 56" closing its distal end. The microcoil 52" has a plurality of apertures 62 along its length, only one of which is shown in the drawings. The apertures 62 provide additional paths for the outflow of the transition material, as shown by the arrows indicated by the numeral 64 in FIG. 10.

A third preferred embodiment of the embolic device is shown in several variations in FIGS. 11–16. Referring first to FIGS. 11 and 12, an embolic device 70 in accordance with this third embodiment is a chain-like structure comprising a plurality of interconnected metal links or segments 72, each of which has a socket 74 at one end and a slotted ball 76 at the other end. Each socket 74 is dimensioned to receive the ball 76 of the adjacent segment 72, the slotted configuration of the balls 76 allowing them to be slightly compressed to fit into the sockets 74. The balls 76 are loosely received in the sockets 74, and the segments 72 are dimensioned so that there is a gap between each adjacent pair. Thus, the entire chain-like structure of the device 70 can be flexibly deformed and twisted much like a microcoil to form the web-like mass 40 when deployed inside an aneurysm by means of the above-described method. When it is desired to rigidify the device 70, an electric current is passed through it, resulting in the fusing of the balls 76 in the sockets 74 by electrolytic corrosion. The electric current can be applied through the deployment tube 16, provided that the deployment tube 16 (including the holding element 24) is made of a conductive metal with suitable electrodes (not shown) that connect the embolic device 70 to a current source (not shown).

A modification of the third embodiment is shown in FIG. 13. An embolic device 70' is a chain-like structure comprising a plurality of interconnected metal links or segments 72', each including a socket 74' at one end and a slotted ball 76' at the other end. The balls 76' are received in the sockets 74' as described above. The modification comprises an annular collar 78 around the socket 74' of each segment 72'. The collar 78 extends axially away from the ball 76' to abut against, or at least be closely adjacent to, the next adjacent segment 72'. The collar 78 is formed of a polymeric transition material that is initially in the soft, compliant state when the device 70' is inserted into an aneurysm, and that is transformed into its rigid or semi-rigid state, in the manner described above, when the aneurysm is filled. Since the collars 78, when rigidified, form interlinking elements between adjacent segments 72', the transformation of the material of the collars 78 rigidities the entire device 70'. A similar effect can be achieved, at some cost savings, by the modified embolic device 70" of FIG. 14, in which only alternating segments 72' are provided with the collar 78.

FIGS. 15 and 16 illustrate still another modification of the third preferred embodiment. In this modification, an embolic device 70''' is a highly-compliant chain-like structure comprising a plurality of interconnected links or segments 72", each of which is hollow. Each of the segments 72" has a slotted, mushroom-shaped head portion 80, and a socket portion 82 that is shaped and dimensioned to receive the head portion 80 of an adjacent segment 72". The hollow segments 72" allow the embolic device 70''' to be inserted into an aneurysm over a guide wire (not shown), if desired. Once the device 70''' is inserted, a transition material 84 (FIG. 16) is injected, while in a flowable state, into the hollow interior of the device 70''', and the transformation of the device 70" from a soft compliant state into its rigid or semi-rigid state can be effected as described above. Alternatively, the segments 72" can be made of a metal and then fused together by electrolytic corrosion, as described above.

For the selection of transition materials which are used in accordance with the present invention to fill the aneurysm in a relatively soft, semi-rigid state as described above, and which thereafter harden to fill the aneurysm in a sufficiently rigid state, the skilled artisan may refer to the self-hardening polymeric materials described in U.S. Pat. No. 5,634,936, the specification of which is incorporated herein by reference. Generally speaking, the materials described in this reference are polymers that, due to the judicious addition of cross-linking agents and/or cross-linking catalysts, are in a semi-rigid state while being introduced through a catheter, and harden only after they have been deposited in the aneurysm. Materials described in U.S. Pat. No. 5,725,568 can also be selected for use in the present invention, and the specification of U.S. Pat. No. 5,725,568 is also incorporated herein by reference.

A presently preferred material for use in the present invention constitutes a microcrystalline wax composition that is of the appropriate semi-rigid consistency a few degrees above body temperature, but becomes sufficiently rigid when cooled to body temperature. As is known, waxes are, generally speaking, fatty acids having more than 12 carbon atoms and a straight alkyl chain. A microcrystalline wax material is readily formulated within the state-of-the-art to have the appropriate transition temperature.

Another presently preferred material for use in the present invention is cellulose acetate polymer that is softened with ethyl lactate or dimethylsulfoxide (DMSO) plasticizer. Still other presently preferred materials are a class of polyurethane based copolymers that are available under the TECOPHILIC trademark from Thermedics Corporation. Specific commercial designations of these copolymers are HP-60D-60, SP-80A-150 and SP-93A-100. These polyurethane-based copolymers are softened with a plasticizer or mixture of plasticizers that are selected primarily from DMSO, ethanol, and ethyl lactate, with DMSO being most suitable for HP-60D-60, and ethanol or ethyl lactate or mixtures thereof for SP-80A-150 and SP-93A-100. The above-noted plasticizers are sufficiently water soluble that after the intimate mixture of polymeric material and plasticizer has been deposited in the aneurysm, percolation of blood gradually washes out the plasticizer from the polymeric material to render it rigid.

A composition that is well-suited for the transition material in the hollow microcoil embolic devices 50' and 50" of FIGS. 7 through 10, and for the transition material 84 of the embolic device 70''' of FIGS. 15 and 16, is cyanoacrylate. The cyanoacrylate rigidifies by polymerization when contacted by vascular blood which seeps into the embolic device 70''' between the segments 72".

In addition to the foregoing, a number of biocompatible polymers and copolymers, such as ethylene vinyl alcohol copolymers, polycarbonate urethane copolymers, and hydrogels may be formulated with a sufficient amount of biocompatible plasticizer, such as DMSO, to render them semi-rigid and suitable for application in the present invention through the catheters described above. Thereafter, these materials harden sufficiently in the aneurysm due to the removal of the plasticizer by percolating blood.

While several preferred embodiments have been described above, as well as a number of variations and modifications, it will be appreciated that other variations and modifications will suggest themselves to those skilled in the pertinent arts. Such variations and modifications are considered to be within the spirit and scope of the invention, as set forth in the claims that follow.

What is claimed is:

1. Apparatus for vascular embolization that is deployable through a microcatheter having an axial lumen, comprising:

a flexible, elongate, hollow deployment tube dimensioned for insertion through the lumen of the microcatheter, the deployment tube having a proximal end and a distal end; and a filamentous embolic device having a proximal end releasably attached to the distal end of the deployment tube, the embolic device being controllably transformable from a soft, compliant state to a rigid or semi-rigid state.

2. The apparatus of claim 1, wherein the embolic device includes a polymeric material that is controllably transformable from a soft, compliant state to a rigid or semi-rigid state.

3. The apparatus of claim 2, wherein the polymeric material is transformable by contact with vascular blood.

4. The apparatus of claim 2, wherein the polymeric material is controllably transformable by contact with a biocompatible liquid that is cooler than vascular blood.

5. The apparatus of claim 3, wherein the polymeric material is mixed with a biocompatible plasticizer that is soluble in vascular blood.

6. The apparatus of claim 3, wherein the polymeric material includes a microcrystalline wax composition.

7. The apparatus of claim 5, wherein the polymeric material is selected from the group consisting of cellulose acetate polymers and polyurethane-based copolymers.

8. The apparatus of claim 7, wherein the plasticizer is selected from a group consisting of dimethylsulfoxide, ethyl lactate, and ethanol.

9. The apparatus of any of claims 2 through 8, wherein the embolic device comprises a continuous extrusion of the polymeric material.

10. The apparatus of claim 3, wherein the embolic device comprises an elongate, flexible microcoil having a hollow interior containing the polymeric material.

11. The apparatus of any of claims 2 through 8, wherein the embolic device comprises an elongate, flexible chain of multiple interlinked segments, at least some of which include an interlinking portion made of the polymeric material.

12. The apparatus of claim 1, wherein the embolic device comprises an elongate, flexible chain of multiple interlinked metal segments, wherein the chain is transformable by electrolytic corrosion.

13. The apparatus of any of claim 3, wherein the embolic device comprises an elongate, flexible chain of multiple interlinked hollow segments filled with the polymeric material.

14. The apparatus of claims 10 or 13, wherein the polymeric material is cyanoacrylate.

15. A vascular embolization device, comprising:

an elongate filamentous element that is controllably transformable from a soft, compliant state to a rigid or semi-rigid state.

16. The device of claim 15, wherein the device includes a portion formed of a polymeric material that is controllably transformable from a soft, compliant state to a rigid or semi-rigid state.

17. The device of claim 16, wherein the polymeric material is transformable by contact with vascular blood.

18. The device of claim 16, wherein the polymeric material is controllably transformable by contact with a biocompatible liquid that is cooler than vascular blood.

19. The device of claim 17, wherein the polymeric material is mixed with a biocompatible plasticizer that is soluble in vascular blood.

20. The device of claim 17, wherein the polymeric material includes a microcrystalline wax composition.

21. The device of claim 19, wherein the polymeric material is selected from the group consisting of cellulose acetate polymers and polyurethane-based copolymers.

22. The device of claim 21, wherein the plasticizer is selected from a group consisting of dimethylsulfoxide, ethyl lactate, and ethanol.

23. The device of any of claims 16 through 22, wherein the filamentous element comprises a continuous extrusion of the polymeric material.

24. The device of claim 17, wherein the filamentous element comprises an elongate, flexible microcoil having a hollow interior containing the polymeric material.

25. The device of any of claims 16 through 22, wherein the filamentous element comprises an elongate, flexible chain of multiple interlinked segments, at least some of which include an interlinking portion made of the polymeric material.

26. The device of claim 15, wherein the filamentous element comprises an elongate, flexible chain of multiple interlinked metal segments, wherein the chain is transformable by electrolytic corrosion.

27. The device claim 17, wherein the filamentous element comprises an elongate, flexible chain of multiple interlinked hollow segments filled with the polymeric material.

28. The apparatus of claims 24 or 27, wherein the polymeric material is cyanoacrylate.

29. A method of embolizing a vascular site, comprising the steps of:
   (a) deploying a catheter so that its distal end is adjacent the vascular site;
   (b) providing an elongate, filamentous embolic device that is controllably transformable from a soft, compliant state to a rigid or semi-rigid state;
   (c) deploying the embolic device through the catheter and into the vascular site so that the embolic device forms a web-like mass in the vascular site; and
   (d) transforming the embolic device from its soft, compliant state to its rigid or semi-rigid state.

30. The method of claim 29, wherein the embolic device has a proximal end and a distal end, and wherein the step of deploying comprises the steps of:
   (c)(1) providing an elongate, flexible deployment tube having a distal end;
   (c)(2) attaching the proximal end of the embolic device to the distal end of the deployment tube;
   (c)(3) inserting the distal end of the deployment tube into the catheter; and
   (c)(4) pushing the deployment tube though the catheter with the assistance of a fluid flowing through the catheter so as to carry the deployment tube and the embolic device through the catheter until the embolic device is deployed in the vascular site; and
   (c)(5) detaching the embolic device from the deployment tube.

31. The method of claims 29 or 30, wherein the embolic device includes a portion made of a polymeric material that is transformable from the soft compliant state to the rigid or semi-rigid state, and wherein the step of transforming is performed by contacting the polymeric portion of the embolic device with vascular blood.

32. The method of claims 29 or 30, wherein the embolic device includes a portion made of a polymeric material that is transformable from the soft, compliant state to the rigid or semi-rigid state, and wherein the step of transforming is performed by contacting the polymeric portion of the embolic device with a biocompatible liquid that is cooler than vascular blood.

33. The method of claims 29 or 30, wherein the embolic device comprises an elongate, flexible chain of multiple interlinked metal segments, and wherein the step of transforming is performed by electrolytic corrosion of the segments.

34. The method of claims 29 or 30, wherein the embolic device has a hollow interior, and wherein the step of transforming includes the steps of:
   (d)(1) injecting a transition material into the interior of the embolic device, the transition material being transformable from a flowable state to a rigid or semi-rigid state by contact with vascular blood; and
   (d)(2) transforming the transition material from the flowable state to the rigid or semi-rigid state through contact with vascular blood.

* * * * *